(12) United States Patent  
Eskuri

(10) Patent No.: US 6,969,395 B2
(45) Date of Patent: Nov. 29, 2005

(54) ELECTROACTIVE POLYMER ACTUATED MEDICAL DEVICES

(75) Inventor: Alan David Eskuri, Hanover, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 618 days.

(21) Appl. No.: 10/213,993

(22) Filed: Aug. 7, 2002

(65) Prior Publication Data

US 2004/0087982 A1    May 6, 2004

(51) Int. Cl.$^7$ ............................................. A61B 17/04
(52) U.S. Cl. ..................................... 606/200; 310/800
(58) Field of Search ...................... 6006/200; 310/800, 310/310, 330

(56) References Cited

U.S. PATENT DOCUMENTS

| | | | |
|---|---|---|---|
| 5,250,167 A | 10/1993 | Adolf et al. | ................ 204/299 |
| 5,268,082 A | 12/1993 | Oguro et al. | ................ 204/282 |
| 5,389,222 A * | 2/1995 | Shahinpoor | ................. 310/309 |
| 5,556,700 A | 9/1996 | Kaneto et al. | .............. 428/332 |
| 5,631,040 A | 5/1997 | Takuchi et al. | ............. 427/100 |
| 5,855,565 A | 1/1999 | Bar-Cohen et al. | ......... 604/104 |
| 6,109,852 A | 8/2000 | Shahinpoor et al. | ........... 414/1 |
| 6,249,076 B1 | 6/2001 | Madden et al. | ............. 310/363 |
| 6,302,905 B1 | 10/2001 | Goldsteen et al. | ........... 623/1.1 |
| 6,309,416 B1 | 10/2001 | Swanson et al. | ........... 623/1.23 |
| 6,514,237 B1 | 2/2003 | Maseda | ....................... 604/533 |

(Continued)

FOREIGN PATENT DOCUMENTS

| | | | |
|---|---|---|---|
| DE | 19936120 A1 | 2/2001 | .......... A61M 25/04 |

(Continued)

OTHER PUBLICATIONS

Worldwide ElectroActive Polymers (Artificial Muscles) Newlsetter, Yoseph Bar-Cohen, Ed., vol.. 3, No. 1, Jun. 2001, pp. 1-14.

(Continued)

*Primary Examiner*—Gary Jackson
(74) *Attorney, Agent, or Firm*—Mayer Fortkort & Williams PC; David B. Bonham, Esq.

(57) ABSTRACT

The present invention is directed to novel apparatus for use in medical procedures relating to tubular body fluid conduits. According to a first aspect of the invention, a filter apparatus is provided for delivery over a guidewire within a tubular body conduit, such as a blood vessel. The filter apparatus comprises: (a) a filter element transformable between a collapsed state and a deployed state, wherein the filter element is adapted to filter particulate matter from fluid within the tubular body conduit while in the deployed state; and (b) a locking member comprising one or more electroactive polymer actuators which switch the locking member between (i) a locking state wherein the locking member securely engages the guidewire and (ii) a release state wherein the locking member is movable along the length of the guidewire. According to a second aspect of the invention, a connector apparatus is provided for use in making an anastomotic connection between first and second tubular fluid conduits in a patient. The connector apparatus comprises: (a) a locking member, which further comprises one or more electroactive polymer actuators that switch the locking member between a locking state and a release state; and (b) a connector body that is configured to permit flow of bodily fluid between the first and second tubular fluid conduits. The connector body has a first portion configured for insertion into an axial end of the first tubular fluid conduit and a second portion configured for insertion through a sidewall of the second tubular fluid conduit. The second portion of the connector body is further configured to securely engage the locking member when the locking member is in the locking state.

16 Claims, 14 Drawing Sheets

U.S. PATENT DOCUMENTS

| | | | |
|---|---|---|---|
| 6,707,236 B2 * | 3/2004 | Pelrine et al. | 310/311 |
| 6,768,246 B2 * | 7/2004 | Pelrine et al. | 310/339 |
| 6,781,284 B1 * | 8/2004 | Pelrine et al. | 310/330 |
| 6,812,624 B1 * | 11/2004 | Pei et al. | 310/800 |
| 6,882,086 B2 * | 4/2005 | Kornbluh et al. | 310/328 |
| 2001/0012951 A1 | 8/2001 | Bates et al. | 606/200 |
| 2002/0004667 A1 | 1/2002 | Adams et al. | 606/200 |
| 2002/0022858 A1 | 2/2002 | Demond et al. | 600/200 |
| 2002/0038132 A1 | 3/2002 | Abrams | 606/200 |
| 2002/0045916 A1 | 4/2002 | Gray et al. | 606/200 |

FOREIGN PATENT DOCUMENTS

| | | | |
|---|---|---|---|
| WO | WO 99/65409 | 12/1999 | A61B 17/32 |
| WO | WO 00/78222 A1 | 12/2000 | A61B 17/00 |
| WO | WO 01/58973 | 8/2001 | |

OTHER PUBLICATIONS

Edwin W. H. Jager et al., "Microfabricating Cojugated Polymer Actuators,"Science, vol. 290, Nov. 24, 2000, pp. 1540-1545.

Electroactive Polymer (EAP) Actuators as Artifical Muscles: Reality, Potential, and Challenges, Yoseph Bar-Cohen, Ed., SPIE Press (2001), Chapter 16, pp. 457-495.

Electroactive Polymer (EAP) Actuators as Artifical Muscles: Reality, Potential, and Challenges, Yoseph Bar-Cohen, Ed., SPIE Press (2001), Chapter 21, pp. 615-659.

Yoseph Bar-Cohen, "Transition of EAP material from novelty to practical applications—are we there yet?," Electroactive Polymer Actuators and Devices, Proceedings of SPIE, vol. 4329, Mar. 5-8, 2001, pp. 1-6.

John D.W. Madden et al., "Polypyrole actuators: modeling and performance," Electroactive Polymer Actuators and Devices, Proceedings of SPIE, vol. 4329, Mar. 5-8, 2001, pp. 72-83.

Ron Pelrine, et al., "Applications of Dielectric Elastomer Actuators," Electroactive Polymer Actuators and Devices, Proceedings of SPIE, vol. 4329, Mar. 5-8, 2001, pp. 335-349.

David L. Brock, "Review of Artificial Muscle based on Contractile Polymers," MIT Artifical Intelligence laboratory, A.I. Memo No. 1330, Nov., 1991, 12 pages.

Electroactive Polymer (EAP) Actuators as Artifical Muscles, Yoseph Bar-Cohen, Ed., SPIE Press (2001), Chapter 7, pp. 193-221.

Electroactive Polymer (EAP) Actuators as Artifical Muscles, Yoseph Bar-Cohen, Ed., SPIE Press (2001), Chapter 1, pp. 3-44.

* cited by examiner

ELECTROACTIVE POLYMER ACTUATED MEDICAL DEVICES

FIELD OF THE INVENTION

The present invention relates to devices for use in medical procedures, and more particularly to electroactive-polymer-containing devices for use in medical procedures concerning tubular body fluid conduits.

BACKGROUND OF THE INVENTION

Numerous medical procedures are known which involve tubular fluid conduits such as blood vessels. One such procedure, known as percutaneous transluminal angioplasty, involves the use of an angioplasty balloon catheter in a minimally invasive treatment to enlarge a stenotic or diseased blood vessel. In order to prolong the positive effects of percutaneous transluminal angioplasty, a stent may be implanted in conjunction with the procedure to provide radial support to the treated vessel. A thrombectomy is another minimally invasive procedure that may be conducted in lieu of a percutaneous transluminal angioplasty. It is a procedure that can be used to remove an entire thrombosis or a sufficient portion of the thrombosis to enlarge the stenotic or diseased blood vessel. Atherectomy is another well-known minimally invasive procedure that mechanically cuts or abrades a stenosis within the diseased portion of the vessel. Ablation therapies are further alternative therapies that use laser or RF signals to superheat or vaporize the thrombosis within the vessel.

During each of the above procedures, there is a risk that dislodged emboli will travel into smaller diameter regions of the vasculature, blocking blood vessels and causing ischemic injury. This problem is especially severe where the emboli are permitted to travel into the coronary arteries and cerebral arteries, and can result in infarction, stroke and even death. Thus, practitioners have approached prevention of escaped emboli through use of a number of techniques, including the capture of emboli in a filter or occlusion device positioned distal to the treatment area.

Emboli filtration devices are known in which filter elements are deployed against the walls of a vessel distal to a stenosis. Such filters typically comprise a polymer or wire filtration element mounted on a distal region of a guide wire or angioplasty catheter. Blood is permitted to flow through the filter while trapping emboli. Once treatment of the stenosis is completed, the filter containing the captured emboli is contracted and withdrawn from the vessel. Examples of prior art filters can be found, for example, in U.S. patent application Pub. No. 2002/0,022,858 A1, U.S. patent application Pub. No. 2002/0,045,916 A1, U.S. patent application Pub. No. 2002/0,004,667 A1, and U.S. patent application Pub. No. 2001/0,012,951 A1, the disclosures of which are hereby incorporated by reference.

In view of the foregoing needs, a novel filtration apparatus, which can be used to remove emboli from blood, for example, is clearly of interest to those skilled in the art.

A second group of procedures involving tubular body fluid conduits are procedures in which an anastomotic connection is made between the conduits. An anastomotic connection, or anastomosis, is a connection that allows body fluid to flow between the lumens of the two conduits that are connected, generally without allowing body fluid to leak from the conduits at the point of connection.

A coronary bypass procedure is one example of a procedure involving an anastomosis. Typically, in order to bypass an obstruction in a patient's coronary artery, a tubular graft supplied with aortic blood may be connected via an anastomosis to the contrary artery downstream from the obstruction. In many cases, the anastomosis is formed between the end of the graft and an aperture in the sidewall of the coronary artery (a so-called end-to-side anastomosis). The graft may be a natural conduit, an artificial conduit, or a combination of natural and artificial conduits (e.g., natural tubing coaxially disposed inside artificial tubing). If natural conduit is used, it may be wholly or partly relocated from elsewhere in the patient (e.g., a wholly relocated saphenous vein or a partly relocated internal mammary artery). More than one anastomosis may be needed. For example, a second anastomosis may be needed between an upstream portion of the graft conduit and the aorta or the coronary artery upstream from the obstruction in that artery. Again, this second anastomosis is frequently an end-to-side anastomosis. Alternatively, no second, upstream anastomosis may be required at all (e.g., if the graft is an only-partly-relocated internal mammary artery).

Currently, the most common technique for making an anastomosis is to manually suture the two tubular body fluid conduits together around an opening between them. Manual suturing is difficult and time-consuming. In the case of coronary artery bypass procedures, one source of difficulty for suturing of an anastomosis may be motion of the heart.

Sutureless anastomosis techniques are known, for example, from U.S. Pat. Nos. 6,309,416 and 6,302,905 assigned to St. Jude Medical Cardiovascular Group, the disclosures of which are hereby incorporated by reference. Both of these references describe techniques in which a connector device is used in providing an anastomosis between two tubular body fluid conduits in a patient. Deployment of such connectors is also significantly less invasive than techniques that require suturing.

In view of the foregoing, a novel apparatus that can be used to make an anastomotic connection in lieu of manual suturing is clearly desirable.

SUMMARY OF THE INVENTION

The present invention is directed to novel apparatus for use in medical procedures relating to tubular body fluid conduits.

According to a first aspect of the invention, a filter apparatus is provided for delivery over a guidewire within a tubular body conduit, such as a blood vessel. The filter apparatus comprises: (a) a filter element transformable between a collapsed state and a deployed state, which is adapted to filter particulate matter from fluid within the tubular body conduit while in the deployed state; and (b) a locking member comprising one or more electroactive polymer actuators which switch the locking member between (i) a locking state wherein the locking member securely engages the guidewire and (ii) a release state wherein the locking member is movable along the length of the guidewire.

In certain preferred embodiments, the locking member is radially expandable and contractible, comprising, for example, a radially expandable and contractible annular member or one or more radially expandable and contractible arms. In some instances, the radially expandable and contractible member engages one or more indentations, for example circumferential groove, in the guidewire.

The filter element comprises a plurality of expandable and collapsible struts in certain preferred embodiments.

The filter apparatus beneficially further comprises a delivery catheter, which is adapted to apply a voltage to the locking member, allowing the locking member to be switched between the locking and release states. In some cases, the delivery catheter is provided with electrical contacts, which correspond to complementary electrical contacts associated with the locking member.

The filter apparatus can also beneficially comprise a tubular sheath that is adapted to receive the filter element while in the collapsed state. For example, the tubular sheath can be slidably disposed along the guidewire, allowing the filter element to be delivered to a deployment position while in the collapsed state. The filter element expands to the deployed state upon removal from the sheath.

The present is also directed to methods of deploying a filter element within a tubular body conduit in a patient using the above filter apparatus. These methods typically comprise the following: (a) advancing the filter apparatus over the guidewire within the tubular body conduit to a deployment position within the tubular body conduit, while the filter element is in the collapsed state; (b) switching the locking member from the release state to the locking state, thereby engaging the locking member with the guidewire; and (c) expanding the filter element to the deployed state within the tubular body conduit.

In preferred embodiments, the filter assembly is advanced over the guidewire while the locking member is in a radially expanded configuration, whereupon the locking member is switched to a radially contracted position to securely engage the filter assembly to the guidewire.

The above apparatus is particularly well adapted for use in procedures involving blood vessels in which particulate matter may be inadvertently dislodged.

One advantage of this first aspect of the present invention is a filtration apparatus is provided which can be used to remove emboli from the blood.

Another advantage of this aspect of the present invention is a filtration apparatus is provided which can be deployed along a guidewire.

According to a second aspect of the present invention, a connector apparatus is provided for use in making an anastomotic connection between first and second tubular fluid conduits in a patient. The connector apparatus comprises: (a) a connector body configured to permit flow of bodily fluid between the first and second tubular fluid conduits, the connector body having a first portion configured for insertion into an axial end of the first tubular fluid conduit and a second portion configured for insertion through a sidewall of the second tubular fluid conduit, and (b) a locking member configured for engagement with the second portion of the connector body. The connector body and/or the locking member comprises one or more electroactive polymer actuators that are configured to switch between a locking state where the locking member and the connector body are securely engaged with one another and a release state where the locking member and the connector body are releasable from one another.

In preferred embodiments, the locking member comprises one or more electroactive polymer actuators that switch the locking member between the locking and release states, and the second portion of the connector body is configured to securely engage the locking member when the locking member is in the locking state.

More preferably, the second portion of the connector body and the locking member are configured such that (a) the second portion can be inserted into the locking member when the locking member is in the release state and (b) the locking member securely engages the second portion when the locking member is in the locking state. For example, in some instances, the locking member comprises a radially expandable and contractible annular member or one or more radially expandable and contractible arms. In these instances, the connector body can be, for example, a tubular structure having a circumferential groove in an outer surface.

In some embodiments, the connector apparatus beneficially further comprises a delivery catheter that is adapted to (a) deliver the locking member to a location within the second tubular fluid conduit where the connector body is inserted through the sidewall of the second tubular fluid conduit and (b) switch the locking member between the release state and the locking state. The delivery catheter can comprise, for example, first and second jaws that are configured to grasp the locking member. The locking member can comprise, for example, first and second electrical contacts that correspond to the grasping positions of the first and second jaws, with a voltage being applied when desired to the contacts through the first and second jaws.

In some embodiments, the connector apparatus beneficially further comprises a tubular sheath that is adapted to receive the delivery catheter and the locking member.

Other embodiments of the present invention are directed to methods of making an anastomotic connection between first and second tubular fluid conduits in a patient using the above connector apparatus. These methods typically comprise the following: (a) inserting the first portion of the connector body into an axial end of the first tubular fluid conduit; (b) inserting the second portion of the connector body through a sidewall of the second tubular fluid conduit; (c) advancing the locking member to a position within the second tubular fluid conduit that is adjacent the second portion of the connector body; and (d) switching the locking member from the release state to the locking state, thereby engaging the locking member with the second portion. Preferably, the tubular fluid conduits are tubular blood conduits. For instance, the first tubular blood conduit can be a tubular graft, while the second tubular blood conduit can be the aorta.

One advantage of this second aspect of the present invention is that an apparatus is provided that can be used to make an anastomotic connection, without the need for a high degree of manual suturing skill.

Another advantage of this aspect of the present invention is that an apparatus is provided that can be used to make an anastomotic connection, even though access to the site of the anastomosis may be limited.

These and other embodiments and advantages of the present invention will become apparent from the following detailed description, and the accompanying drawings, which illustrate by way of example the features of the invention.

DETAILED DESCRIPTION OF PREFERRED EMBODIMENTS OF THE INVENTION

Figure 1:
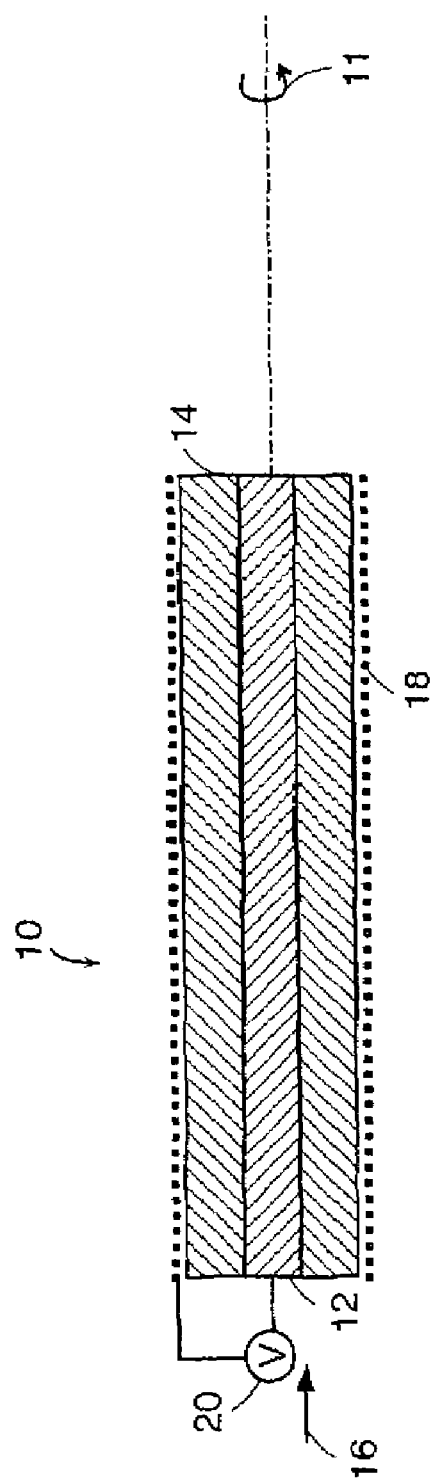
FIG. 1 is a schematic cross-sectional view of a known electroactive polymer actuator.

According to a first aspect of the present invention, a filter apparatus is provided for use in minimally invasive procedures within a tubular body fluid conduit, such as vascular or other procedures where the practitioner desires to capture material that may be dislodged during the procedure.

One specific embodiment of a filter assembly 110 in accordance with the present invention will now be described with reference to FIG. 2. The filter assembly 110 is disposed along guidewire 120. The filter assembly 110 includes a filter element 112, which is typically formed from a suitable mesh or porous material that will filter particulate material (e.g., emboli from blood) while permitting sufficient perfusion therethrough. Such filter elements 112 are well known in the art.

In the embodiment shown, the filter element 112 is provided with an expandable support frame for outwardly deploying the filter element 112 in a fashion such that it substantially fills the cross section of the body fluid conduit within which it is deployed. In the embodiment illustrated in FIG. 2, the expandable support frame includes a series of struts 115, which are preferably formed from a bendable material having a shape memory. A metal (e.g., stainless steel or nitinol), a polymer, or any other suitable material can be used in the construction of struts 115 so long as the material is sufficiently resilient to properly deploy the filter element 112.

The particular struts 115 that are illustrated extend from the proximal and distal ends of a tube 116. The proximal end of the tube 116 is adjacent a guidewire engagement member 118. The filter element 112 is secured to the struts 115 and to the distal end of tube 116 in the embodiment shown.

In other embodiments, the filter element 112 is formed from a material that has a shape memory, eliminating the need for a separate support frame. For example, the filter element 112 can be woven from filaments of material having a shape memory, which can be expanded upon deployment, for example, a shape-memory metal, such as nitinol or stainless steel, or a non-metallic material that is sufficiently resilient to provide a self-supporting filter assembly. To enhance visualization of the braided filter, at least one of the filaments may be a wire that is made of, or plated with, a radiopaque metal such as gold, platinum, tungsten or alloys thereof.

The filter assembly 110 further includes a guidewire engagement member 118. The guidewire engagement member 118 comprises an electroactive polymer actuator. Actuators based on electroactive polymers have a number of advantageous attributes, including small size, large force and strain, low cost and ease of integration.

Electroactive polymers, members of a family of plastics referred to as "conducting polymers," are a class of polymers characterized by their ability to change shape in response to electrical stimulation. They typically structurally feature a conjugated backbone and have the ability to increase electrical conductivity under oxidation or reduction. Some common electroactive polymers are polyaniline, polysulfone, polypyrrole and polyacetylene.

These materials are typically semi-conductors in their pure form. However, upon oxidation or reduction of the polymer, conductivity is increased. The oxidation or reduction leads to a charge imbalance that, in turn, results in a flow of ions into the material in order to balance charge. These ions, or dopants, enter the polymer from an ionically conductive electrolyte medium that is coupled to the polymer surface. The electrolyte may be, for example, a gel, a solid, or a liquid. If ions are already present in the polymer when it is oxidized or reduced, they may exit the polymer.

It is well known that dimensional changes may be effectuated in certain conducting polymers by the mass transfer of ions into or out of the polymer. For example, in some conducting polymers, the expansion is due to ion insertion between chains, whereas in others interchain repulsion is the dominant effect. Thus, the mass transfer of ions both into and out of the material leads to an expansion or contraction of the polymer.

Referring now to FIG. 1, an actuator 10 is shown schematically in cross-section. Active member 12 of actuator 10 has a surface coupled with electrolyte 14 and has an axis 11. Active member 12 includes an electroactive polymer that contracts or expands in response to the flow of ions out of, or into, the active member 12. Ions are provided by electrolyte 14, which adjoins member 12 over at least a portion, and up to the entirety, of the surface of active member 12 in order to allow for the flow of ions between the two media. Many geometries are available for the relative disposition of member 12 and electrolyte 14. In accordance with preferred embodiments of the invention, member 12 may be a film, a fiber or a group of fibers, or a combination of multiple films and fibers disposed so as to act in concert for applying a tensile force in a longitudinal direction substantially along axis 11. The fibers may be bundled or distributed within the electrolyte 14.

Active member 12 includes an electroactive polymer. Many electroactive polymers having desirable tensile properties are known to persons skilled in the art. In accordance with certain embodiments of the invention, active member 12 is a polypyrrole film. Such a polypyrrole film may be synthesized by electrodeposition according to the method described by M. Yamaura et al., "Enhancement of Electrical Conductivity of Polypyrrole Film by Stretching: Counterion Effect," Synthetic Metals, vol. 36, pp.209–224 (1988), which is incorporated herein by reference. In addition to polypyrrole, any conducting polymer that exhibits contractile or expansile properties may be used within the scope of the invention.

Electrolyte 14 may be, for example, a liquid, a gel, or a solid, so long as ion movement is allowed. Moreover, where the electrolyte 14 is a solid, it should move with the active member 12 and should not be subject to delamination. Where the electrolyte 14 is a gel, it may be, for example, an agar or polymethylmethacrylate (PMMA) gel containing a salt dopant. Where the electrolyte is a liquid, it may be, for example, a phosphate buffer solution. The electrolyte is preferably non-toxic in the event that a leak occurs in vivo.

Counter-electrode 18 is in electrical contact with electrolyte 14 in order to provide a return path for charge to a source 20 of potential difference between member 12 and electrolyte 14. Counter-electrode 18 may be any electrical conductor, for example, another conducting polymer, a conducting polymer gel, or a metal such as gold or platinum. Counter-electrode 18 is in the form of a coil in FIG. 1, but other forms such as foils and so forth are possible.

In order to activate actuator 10, a current is passed between active member 12 and counter-electrode 18, inducing contraction or expansion of member 12.

Additionally, the actuator may have a flexible skin for separating the electrolyte from an ambient environment.

Additional information regarding the construction of actuators, their design considerations, and the materials and components that may be employed therein, can be found, for example, in U.S. Pat. No. 6,249,076, assigned to Massachusetts Institute of Technology, and in Proceedings of the SPIE, Vol. 4329 (2001) entitled "Smart Structures and Materials 2001: Electroactive Polymer and Actuator Devices (see, in particular, Madden et al, "Polypyrrole actuators: modeling and performance," at pp. 72–83), both of which are hereby incorporated by reference in their entirety.

The electroactive polymer actuators can be provided in an essentially infinite array of configurations as desired, including planar actuator configurations, cylindrical actuator configurations (e.g., see the actuator illustrated in FIG. 1), and so forth. In one preferred embodiment, the ends of an actuator like that of FIG. 1 are adjoined, forming a radially expandable and contractible ring.

Figure 3:
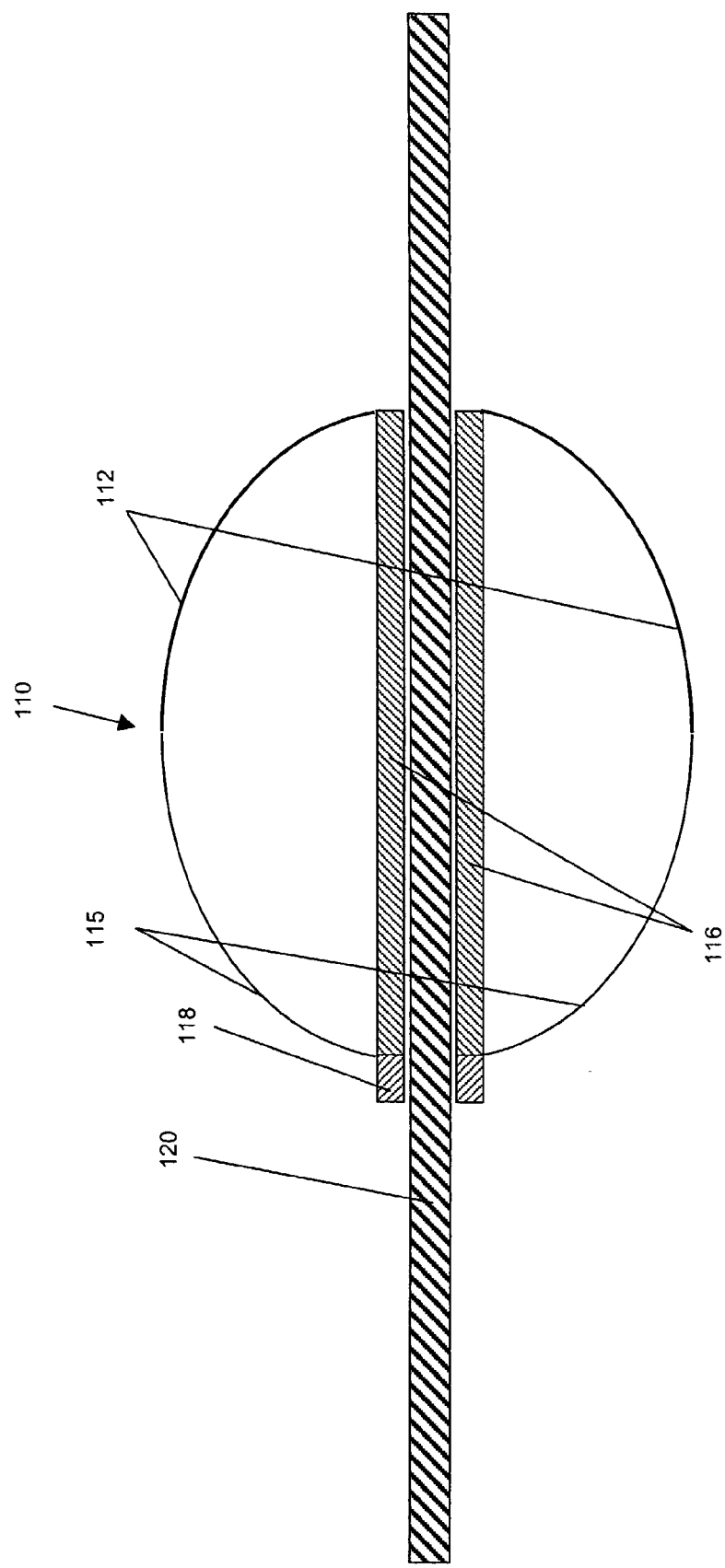
FIGS. 3 and 4 are schematic cross-sectional views of the filter assembly of FIG. 2, in which the guidewire engagement member of the filter assembly is in released and locked states, respectively, in accordance with an embodiment of the present invention.
Figure 4:
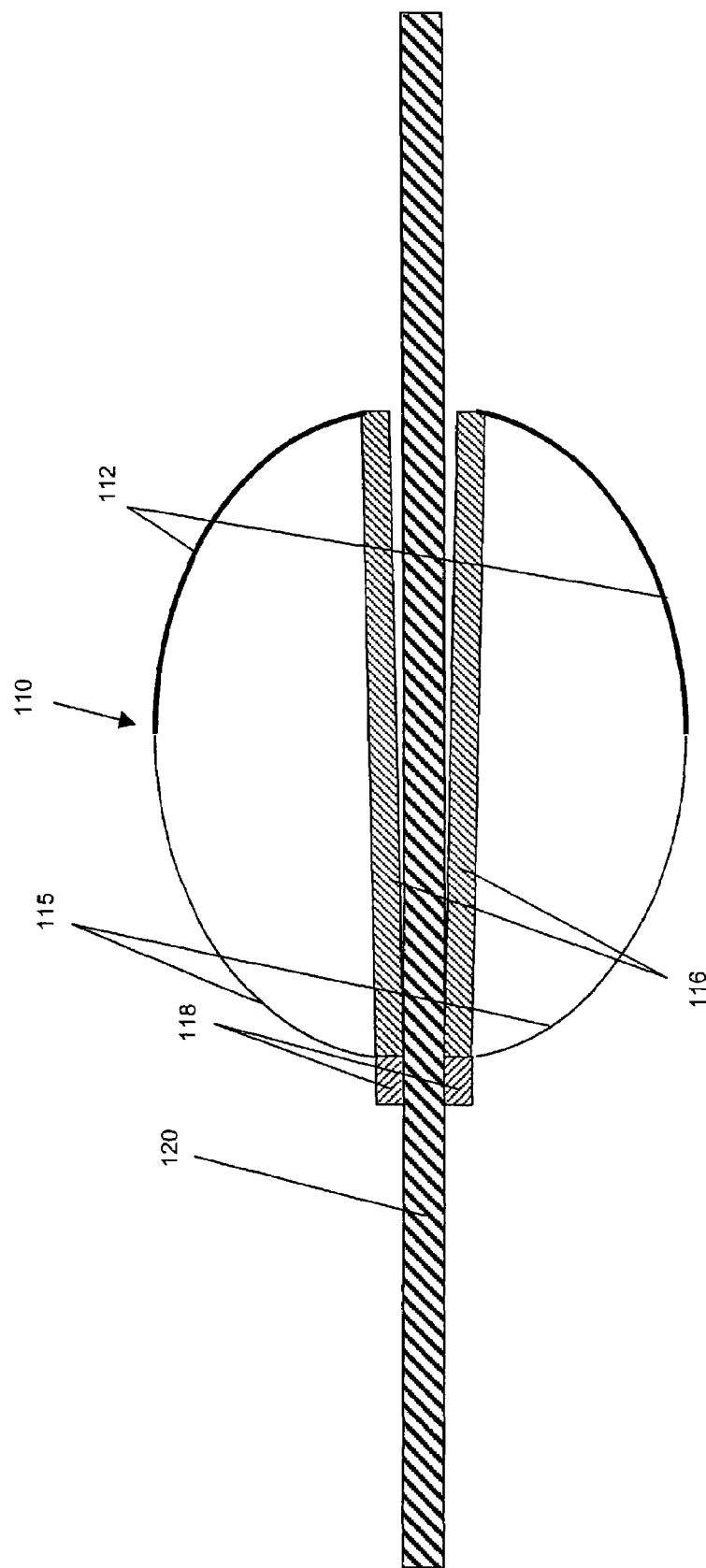

Referring again to FIG. 2, the guidewire engagement member 118 can be formed from such a ring, among other configurations. Cross-sectional views of the filter apparatus of FIG. 2 are illustrated in FIGS. 3 and 4. The guidewire engagement member 118 is in a radially expanded configuration in FIG. 3. In contrast, the guidewire engagement member 118 is in a radially contracted configuration in FIG. 4. When in the radially expanded configuration, the guidewire engagement member 118 permits axial movement between the filter assembly 110 and the guidewire 120. When in the radially contracted configuration, on the other hand, the guidewire engagement member 118 securely grasps the guidewire 120, preventing further relative axial movement between the filter assembly 110 and the guidewire 120.

It is noted that the tube 116 in FIGS. 3 and 4 is illustrated as being deformed during radial contraction of the guidewire engagement member 118. However, in other embodiments deformation can occur solely within the guidewire engagement member 118, within an additional piece inserted between the tube 116 and the guidewire engagement member 118, and so forth.

Figure 2:
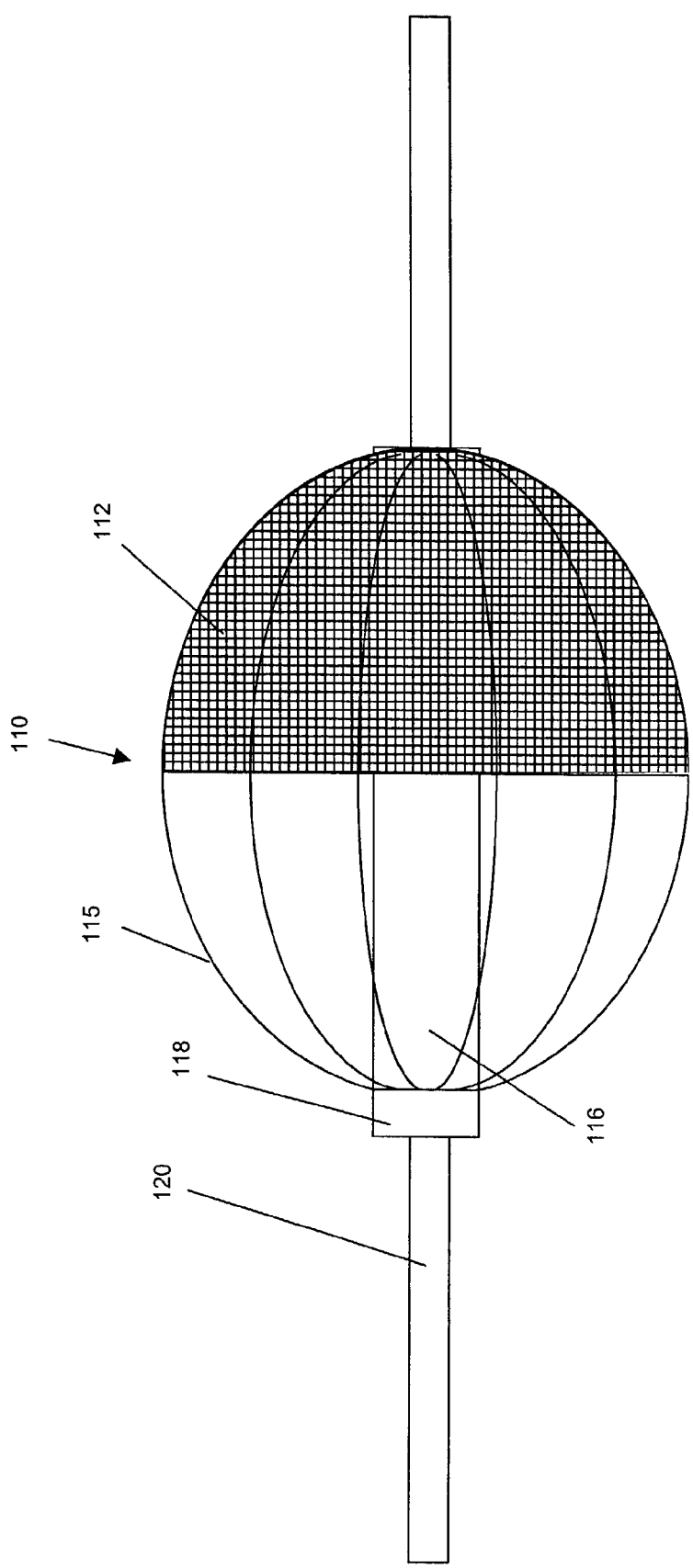
FIG. 2 is a schematic illustration of a guidewire-deployable filter assembly, in accordance with an embodiment of the present invention.
Figure 5:
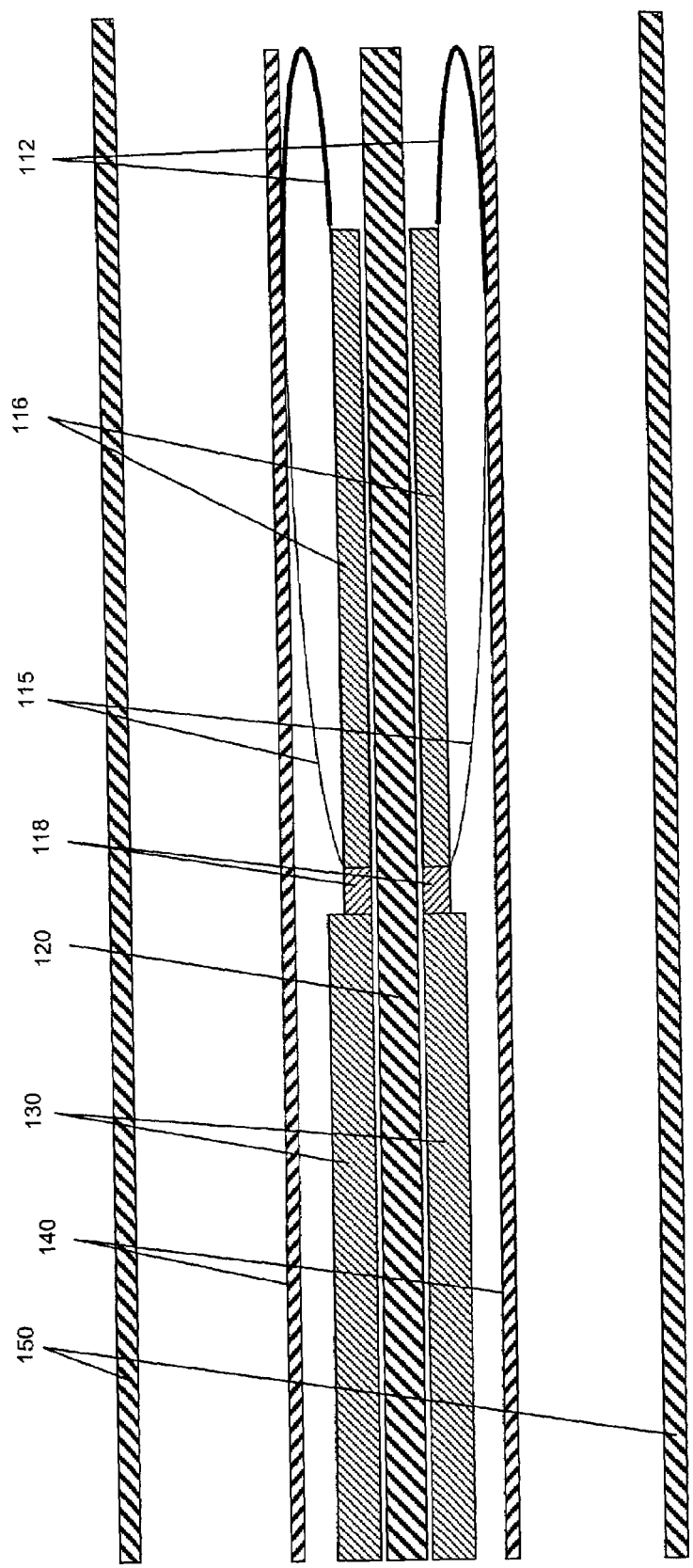
FIGS. 5 and 6 are schematic cross-sectional views illustrating the deployment of the filter assembly of FIG. 2 within a tubular body fluid conduit with the assistance of a sheath and delivery catheter, in accordance with an embodiment of the present invention.
Figure 6:
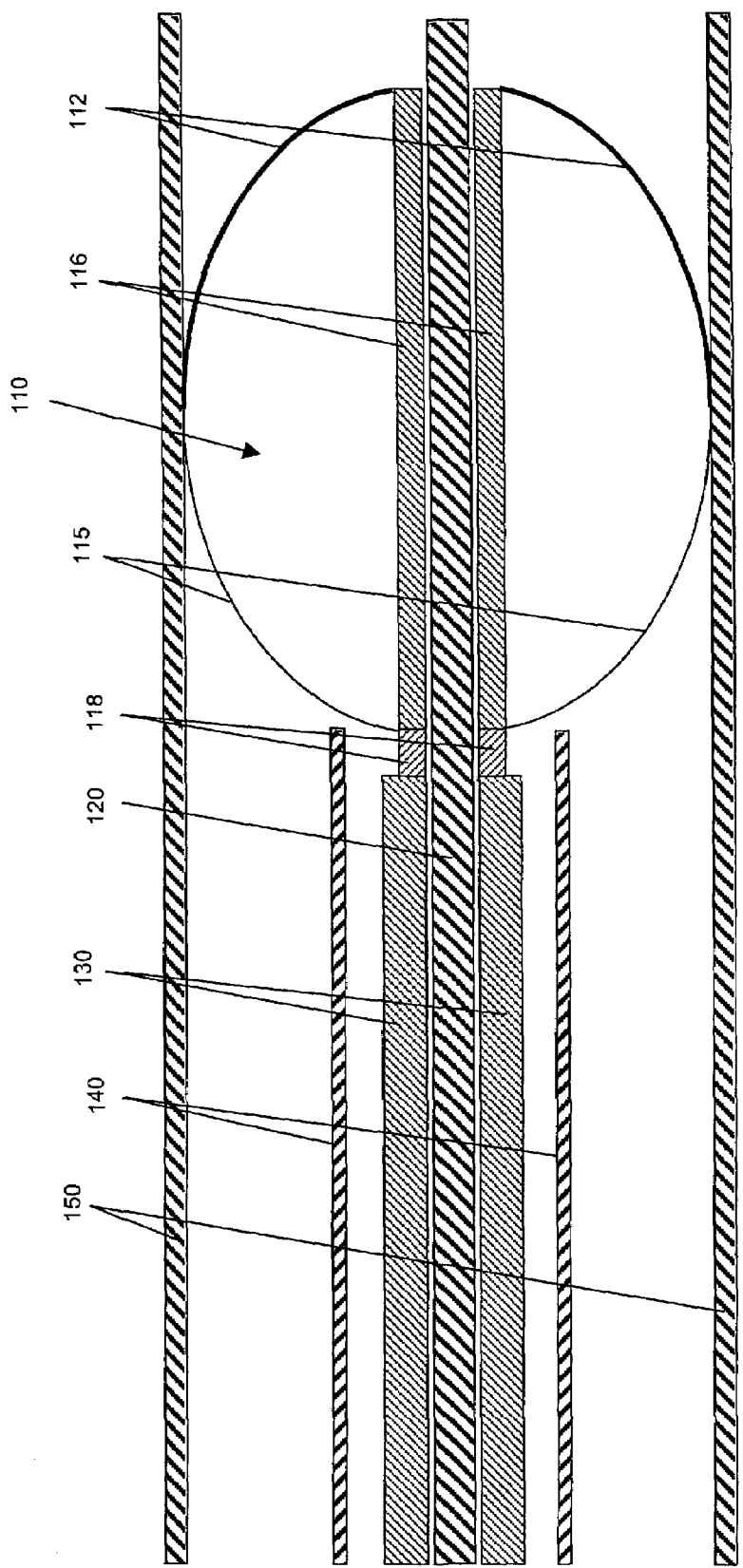

Referring now to FIGS. 5 and 6, the filter assembly of FIG. 2 can be delivered, deployed and retrieved using guidewire 120, delivery catheter 130, and sheath 140, which is slidable over filter assembly. During delivery and retrieval, the filter assembly is collapsed within sheath 140 as shown in FIG. 5. When the filter assembly is extended beyond the sheath 140, the filter assembly is released as shown in FIG. 6.

The filter assembly 110 is concentric with the guidewire 120. As a result, when the filter element 112 is fully deployed, as in FIG. 6, the filter's outer edge will contact the inner surface of the tubular body fluid conduit 150 within which it is deployed, preventing particular matter such as emboli from escaping past the filter element 112.

Referring again to FIG. 5, the mechanism for deploying the filter assembly includes delivery catheter 130 and sheath 140. The sheath 140 is sized to travel over the delivery catheter 130 and guidewire 120 and to receive the filter assembly, which is collapsed within sheath 140 as shown in FIG. 5. In operation, the sheath 140, delivery catheter 130, and filter assembly are routed over the guidewire 120 to the area of interest. Filter assembly 110 and sheath 140 are positioned past, or downstream, of the area of interest.

Figure 8:
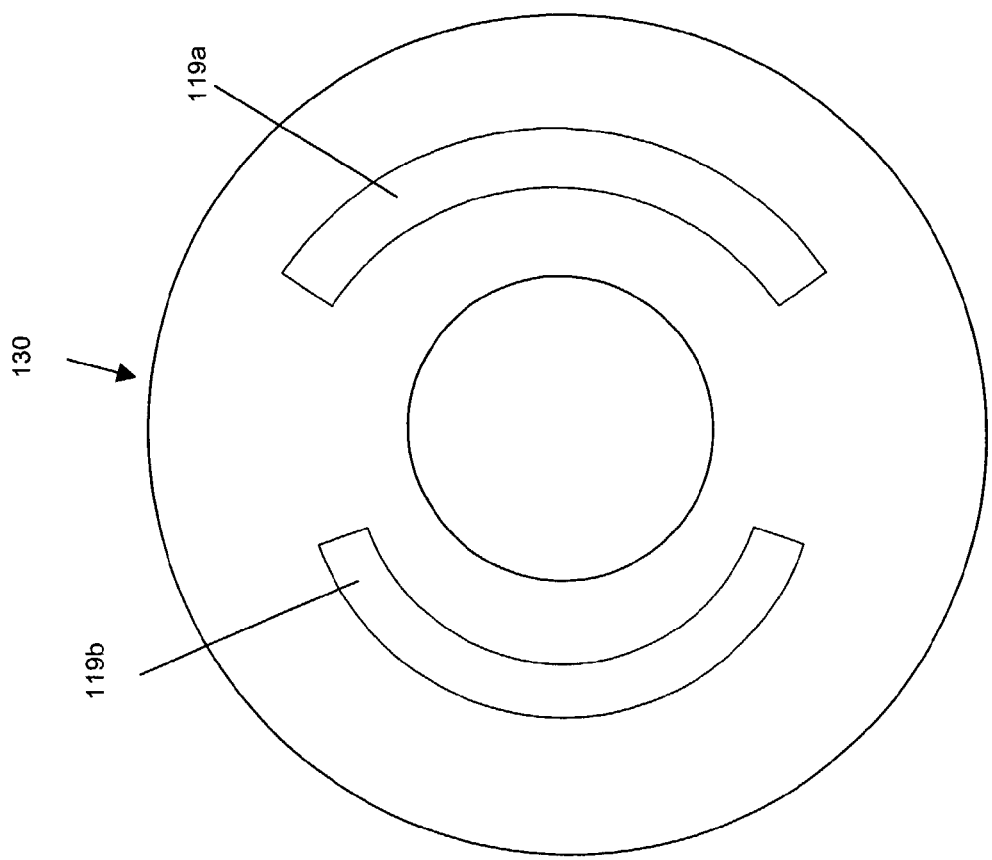
FIGS. 7 and 8 are schematic end views of a guidewire engagement member and delivery catheter, respectively, in accordance with an embodiment of the present invention.
Figure 7:
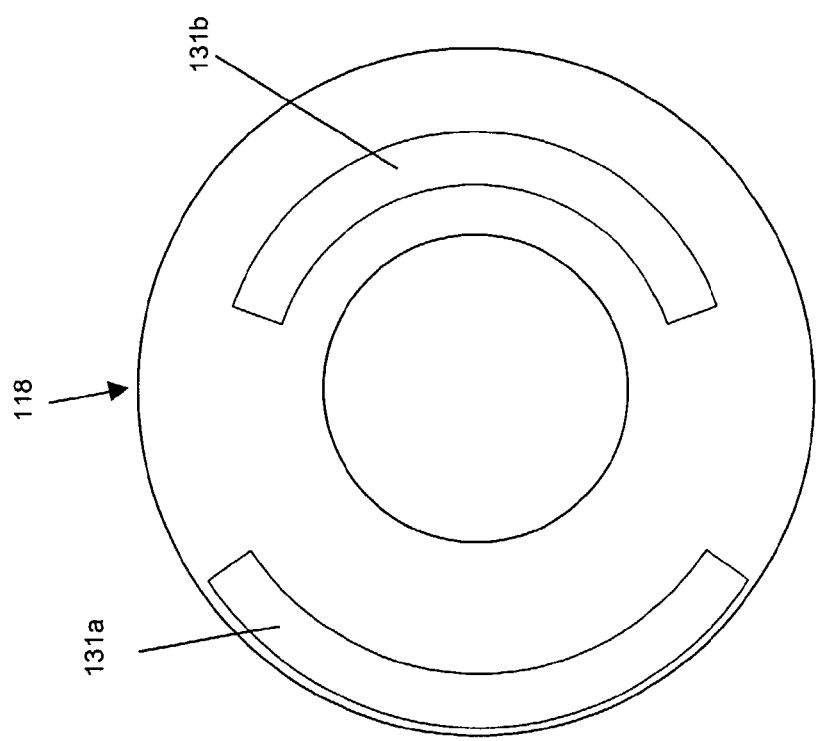

The delivery catheter 130 is configured to provide a voltage to the guidewire engagement member 118 appropriate to place the guidewire engagement member 118 in either an expanded or a contracted state. For example, referring now to FIG. 8, which illustrates a distal end view of delivery catheter 130, it can be seen that the distal end of the delivery catheter 130 can be provided with electrical contacts 131a and 131b. A corresponding (mirror image) pair of contacts 119a, 119b can also be provided on the proximal end of the guidewire engagement member 118 as illustrated in the end view of FIG. 7. One contact 119a is in electrical communication with active member(s) within the guidewire engagement member 118, while the other contact 119b is in electrical communication with the counter-electrode(s) within the guidewire engagement member 118.

The filter assembly can be deployed in a number of ways. For example, the filter assembly 110, delivery catheter 30 and sheath 140 can be routed over the guidewire 120 to a desired position. During advancement, the guidewire engagement member 118 is in a radially expanded state. Beneficially, the electroactive polymer selected will be of the type that is in an expanded state upon application of a potential and a contracted state upon interruption of that potential. After the desired position is reached, the potential is interrupted, resulting in radial contraction of the guidewire engagement member 118, securely engaging the filter assembly 110 with the guidewire 120. The catheter 130 can be withdrawn at this time, if desired.

At this point, the filter assembly 110 can be deployed by retracting the position of the sheath 140, relative to the guidewire 120 and filter assembly 110 (which is now secured to the guidewire). Once the sheath 140 is withdrawn relative to the filter assembly 110, the struts 115 resume their unrestrained positions, and filter element 112 expands to fill the cross-sectional area of the tubular fluid conduit 150. The sheath 140 is typically completely withdrawn at this point.

Subsequently, an appropriate treatment device can be routed over the guide wire to the treatment area. During and after the treatment, for example, an angioplasty, atherectomy or a similar procedure, emboli can be dislodged. These emboli will travel downstream and be captured by filter element 112. The treatment device is removed after the procedure. The sheath 140 can then be re-advanced over the guidewire 120 to the filter assembly 110. The sheath 140 is then pushed over the filter assembly 110, compressing the filter 112 within sheath 140. Finally, the delivery catheter 130 is inserted over the guidewire 120. Upon reaching the guidewire engagement member 118, a voltage is applied which reverts the engagement member 118 to its expanded state, releasing filter assembly 110 from the guidewire 120. Subsequently, the filter assembly 110, delivery catheter 130 and sheath 140 are removed from the patent. The filter assembly 110 is withdrawn with the sheath 140, due to the frictional forces that exist between these two elements arising from the outward pressure exerted by the struts 115 on the sheath 140.

In the above removal procedure, the filter assembly 110 is removed independently of the guidewire 120. In an alternative removal procedure, the sheath 140 is advanced over the guidewire 120 to the filter assembly 110, whereupon the sheath 140 is pushed over the filter assembly 110, compressing the filter 112 within sheath 140. Subsequently, the filter assembly 110, guidewire 120 and sheath 140 are removed from the patent.

Figure 9:
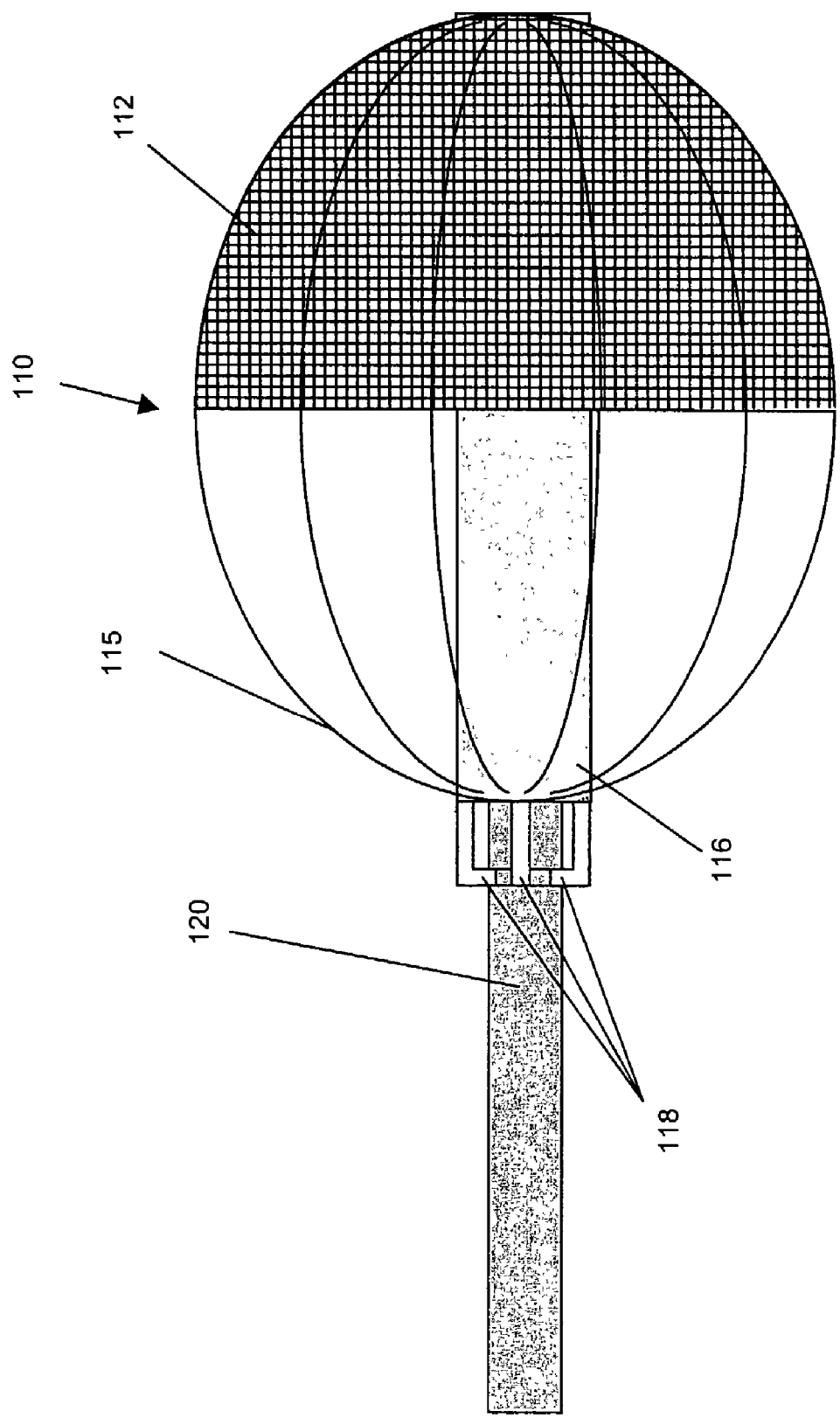
FIG. 9 is a schematic illustration of a guidewire-deployable filter assembly, in accordance with another embodiment of the present invention.
Figure 10:
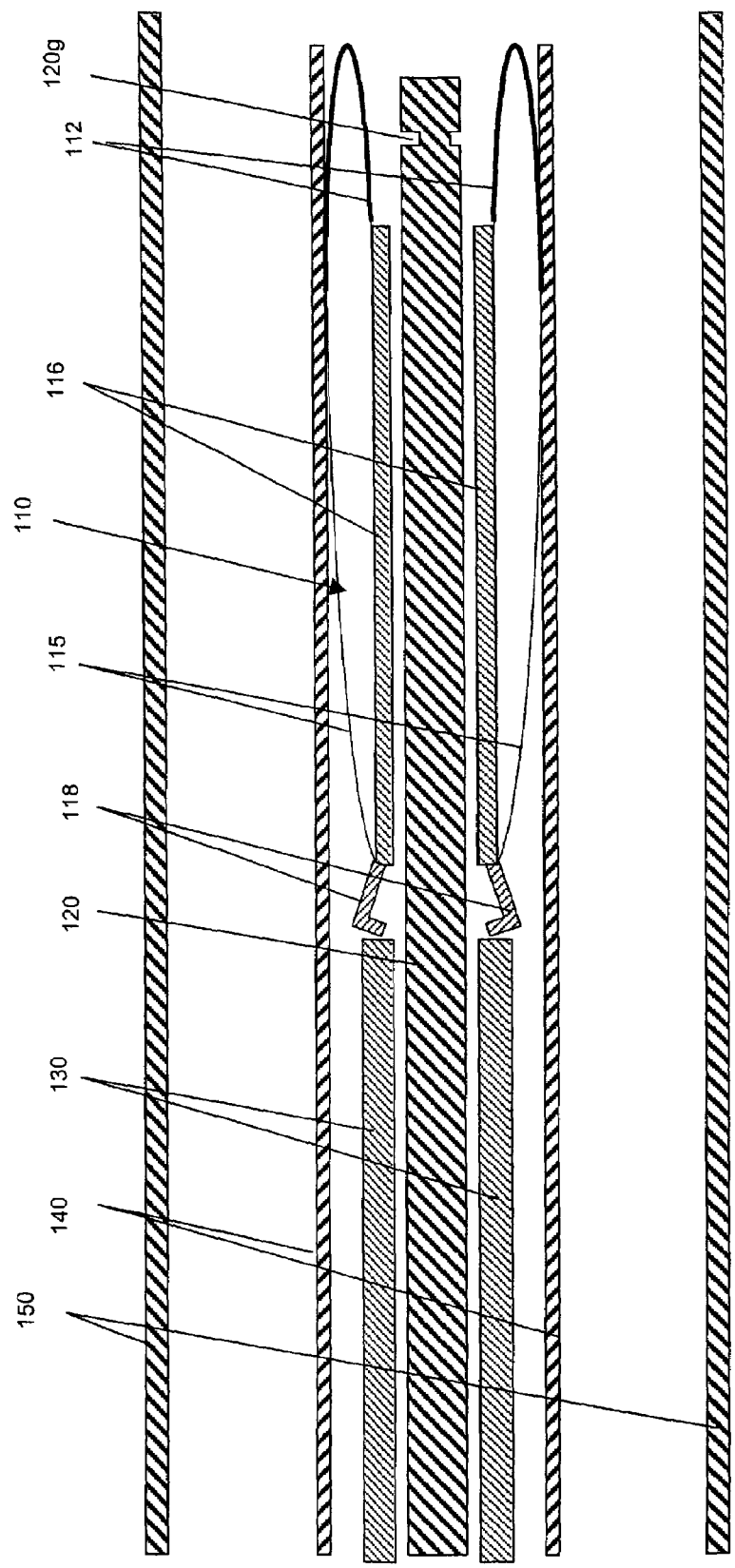
FIG. 10 is a schematic cross-sectional view illustrating the deployment of the filter assembly of FIG. 9 within a tubular body fluid conduit with the assistance of the a sheath and delivery catheter, in accordance with an embodiment of the present invention.

The guidewire engagement member 118 in the above embodiments is provided in a radially expandable and contractile configuration. However, essentially any configuration that is capable of securely engaging the guidewire can be used. For example, the engagement member 118 can include one or more (more preferably, 3 or more) radially expandable and contractible engagement "arms" as illustrated in FIG. 9. Electroactive polymer actuators that are based radially expanding and contracting arms are known. See, e.g., Electroactive Polymer (EAP) Actuators as Artificial Muscles, Yoseph Bar-Cohen, Ed., SPIE Press (2001), Chapter 21("EAP Applications, Potential, and Challenges"), pp. 615–659. The dashed lines in FIG. 9 illustrate the "arms" of the guidewire engagement member 118 in an expanded configuration. In the embodiment shown, the arms engage a groove in the guidewire 120, when in a radially contracted state. This groove 120g can be better seen from the cross-section of FIG. 10, which illustrates the advancement of the filter assembly 110 of FIG. 9, along with delivery catheter 130 and sheath 140 through tubular body conduit 150. Upon reaching the end of guidewire 120, the arms of the guidewire engagement member 118 are radially contracted to engage the groove 120g of guidewire 120.

According to another aspect of the present invention an anastomosis connector is provided for use in establishing anastomotic connections between tubular body fluid conduits.

Figure 11A:
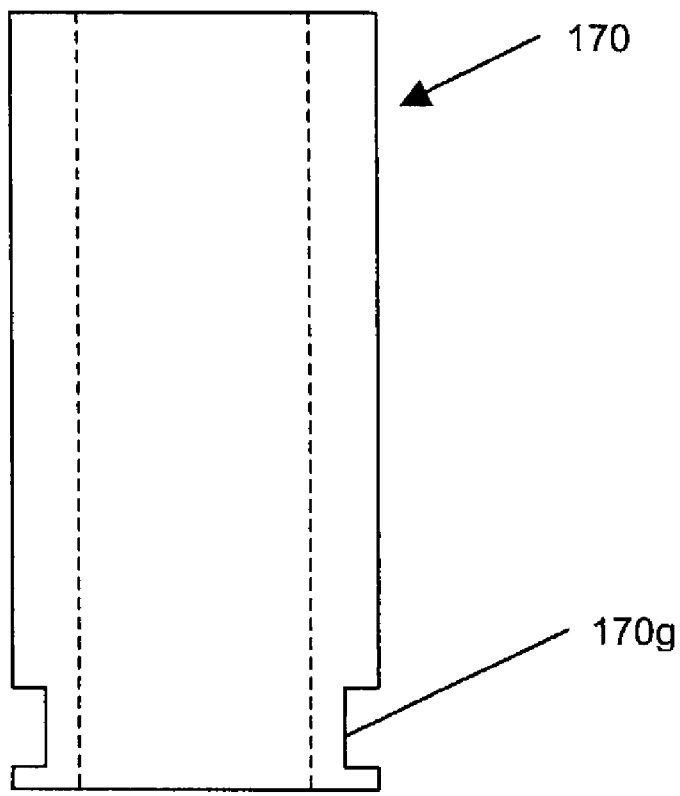
FIGS. 11A and 11B are schematic side and end views, respectively, of an anastomosis connector body, in accordance with an embodiment of the present invention.
Figure 11B:
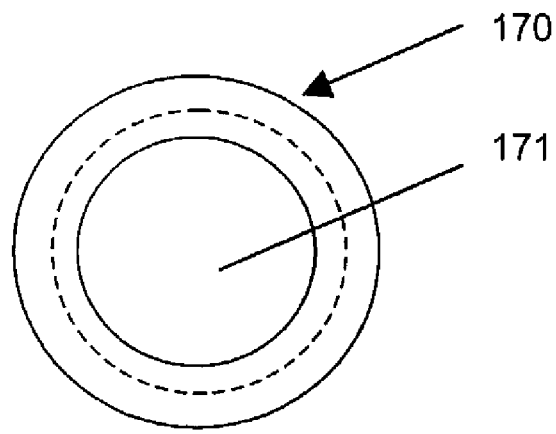

One anastomosis connector, in accordance with an embodiment of the present invention, is provided in FIGS. 11A–11B and 12A–12B. FIG. 11A is a side view of a generally tubular connector body 170 having a groove 170g formed around the outer circumference proximate one end of the connector body 170. FIG. 11B is an axial end view of the connector body 170 of FIG. 11A, illustrating an inner through-hole 171. Inner through-hole 171 from FIG. 11B is illustrated in FIG. 11A using dashed (hidden) lines. Groove 170g from FIG. 11A is illustrated by a dashed line in FIG. 11B.

Figure 12A:
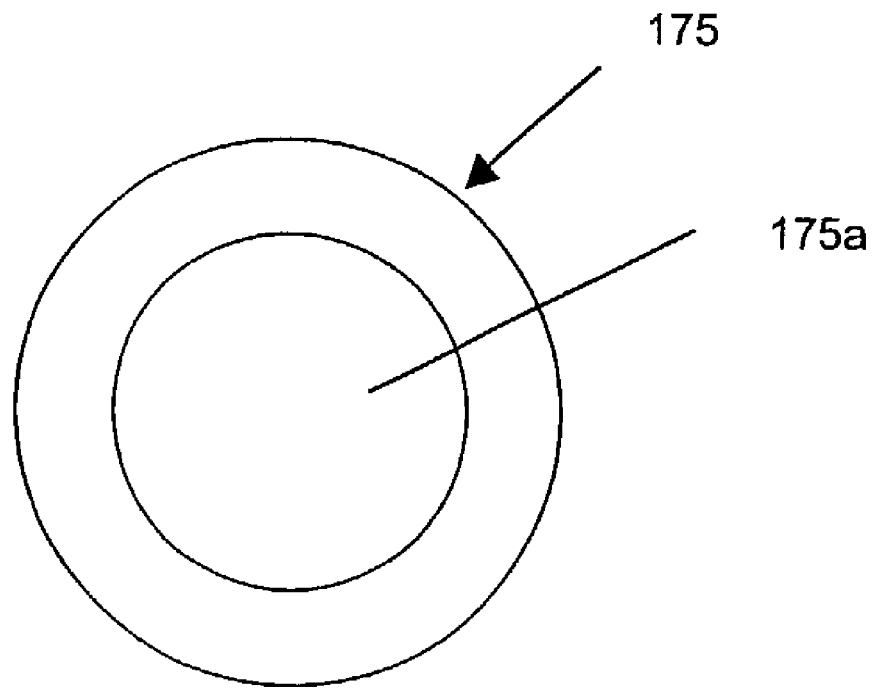
FIGS. 12A and 12B are schematic side and end views, respectively, of an anastomosis connector engagement member, in accordance with an embodiment of the present invention.
Figure 12B:
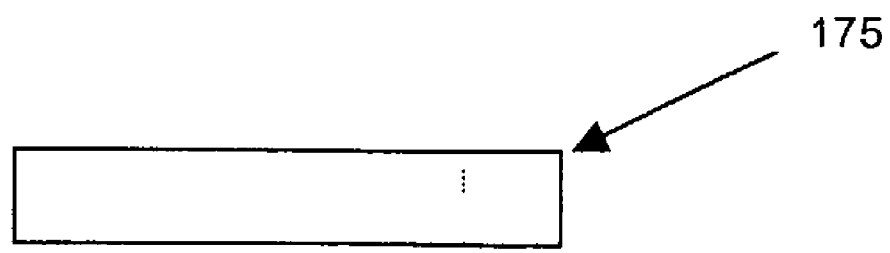

An axial end view of a generally annular connector engagement member 175 having an inner aperture 175a is illustrated in FIG. 12A. A side view of connector engagement member 175 is presented in FIG. 12B, with aperture 175a indicated by dashed lines.

Similar to the guidewire engagement member 118 discussed above, the connector engagement member 175 preferably comprises one or more electroactive polymer actuators such that the connector engagement member 175 is radially expandable and contractible. In use, the connector engagement member 175 is first placed in a radially expanded configuration, preferably by applying a potential to the electroactive polymer actuator(s) in connector engagement member 175. This allows the axial end of the connector body 170 to be inserted into the inner aperture 175a of connector engagement member 175 to a position where the connector engagement member 175 is concentric with the groove 170g of the connector body 170. At this point, the connector engagement member 175 is placed in a radially contracted configuration, for example, by interrupting the voltage that was previously applied to the electroactive polymer actuator(s) in connector engagement member 175. Upon interrupting the voltage, the connector engagement member 175 radially contracts, becoming seated within groove 170g.

Figure 13:
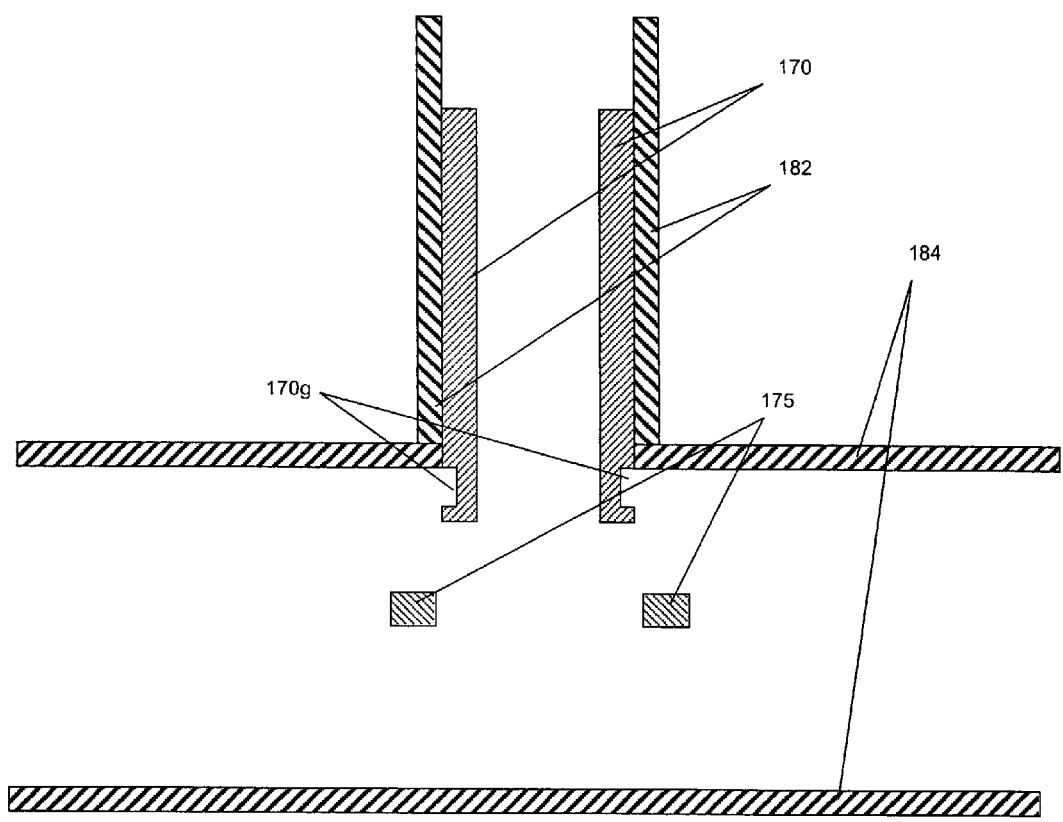
FIGS. 13 and 14 are schematic cross-sectional views illustrating the use of the anastomosis connector body of FIGS. 11A and 11B and the anastomosis connector engagement member of FIGS. 12A and 12B in performing an end-to-side anastomosis procedure, in accordance with an embodiment of the present invention.

An end-to-side anastomosis procedure will now be described using the anastomosis connector of FIGS. 11A–B and 12A–B. With reference now to FIG. 13, the connector body 170 is first attached to one of the body fluid conduits to be connected. As a specific example, the connector body 170 may be inserted into the end portion of a graft conduit 182, which may be, for example, a natural conduit, an artificial conduit, or a combination of natural and artificial conduits (e.g., natural tubing coaxially disposed inside artificial tubing). If natural conduit is used, it may be wholly or partly relocated from elsewhere in the patient (e.g., a relocated saphenous vein). The graft conduit 182 can be secured to the connector body 175 in a number of ways, including suturing, for example, to a mesh or weave type covering (not illustrated) on the connector body 175 or using an appropriate adhesive.

A hole is then formed in the side of the other of the body fluid conduit to be connected. For example, this body fluid conduit may be the aorta 184 of a patient, and the hole may be formed using an aortic punch. Once the hole is formed, the exposed portion of the connector body 170 (i.e., the portion containing groove 170g, which has not been inserted into graft conduit 182) is inserted into the hole up to the point where the axial end of the graft conduit 182 abuts the side of the aorta 184 in this illustration. This can be seen from the cross-section illustrated in FIG. 13.

Meanwhile, connector engagement member 175 is advanced within the aorta 184 to the point where it is in the vicinity of connector body 170.

Figure 15:
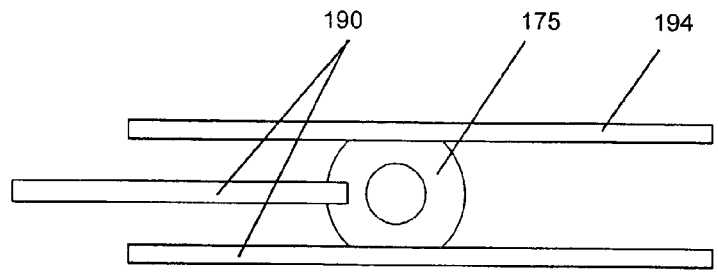
FIGS. 15 and 16 are schematic diagrams illustrating the deployment of the anastomosis connector engagement member of FIGS. 12A and 12B from a sheath via a delivery catheter that comprises forceps, in accordance with an embodiment of the present invention.

Referring now to FIG. 15, according to one embodiment of the invention, the connector engagement member 175 is advanced using a sheath 175 and a delivery catheter, generally designated 190, which contains forceps. Connector engagement member 175 can be partially collapsed and placed within sheath 194. Connector engagement member is held in place by forceps of the delivery catheter 190.

Figure 17:
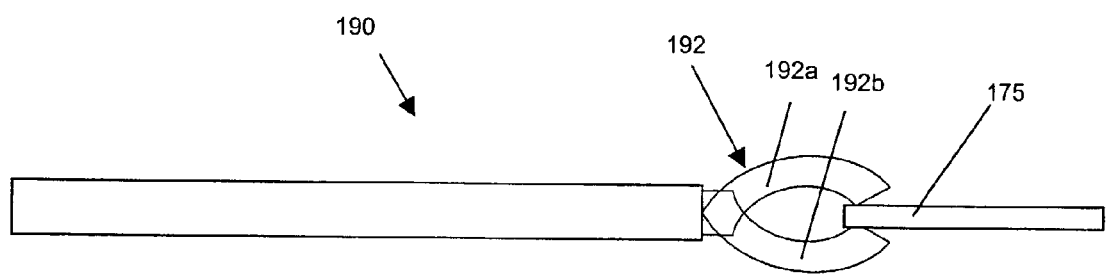
FIG. 17 is an illustration of the anastomosis connector engagement member of FIGS. 12A and 12B while being gripped by a delivery catheter that comprises forceps, in accordance with an embodiment of the present invention.
Figure 18:
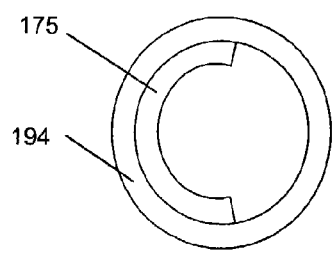
FIG. 18 is a schematic end view of the anastomosis connector engagement member and sheath of FIG. 15, in accordance with an embodiment of the present invention.

FIG. 18 is a schematic end view (delivery catheter is not illustrated) illustrating the sheath 194 and partially collapsed connector engagement member 175 of FIG. 15. FIG. 17 is a schematic illustration of connector engagement member 175 being griped by forceps 192 of delivery catheter 190. The forceps 192 are designed to apply a voltage to connector engagement member 175. For example, a voltage can applied across jaws 192a and 192b of forceps 192, which are placed in electrical contact with contacts (not shown) on the top and bottom surfaces of the connector engagement member 175.

Figure 16:
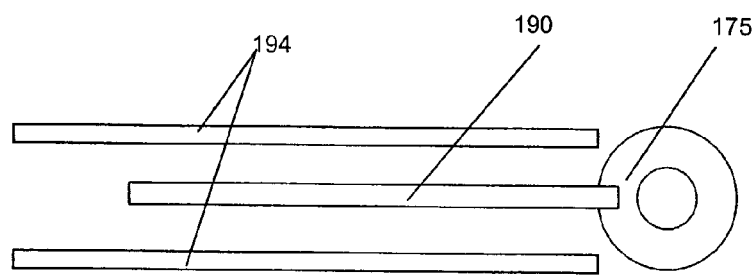

Once the sheath 194, connector engagement member 175 and delivery catheter 190 of FIG. 15 reach the desired destination within the body fluid conduit, the delivery catheter 190 and connector engagement member 175 are advanced relative to sheath 194 as illustrated in FIG. 16, freeing connector engagement member 175.

Figure 14:
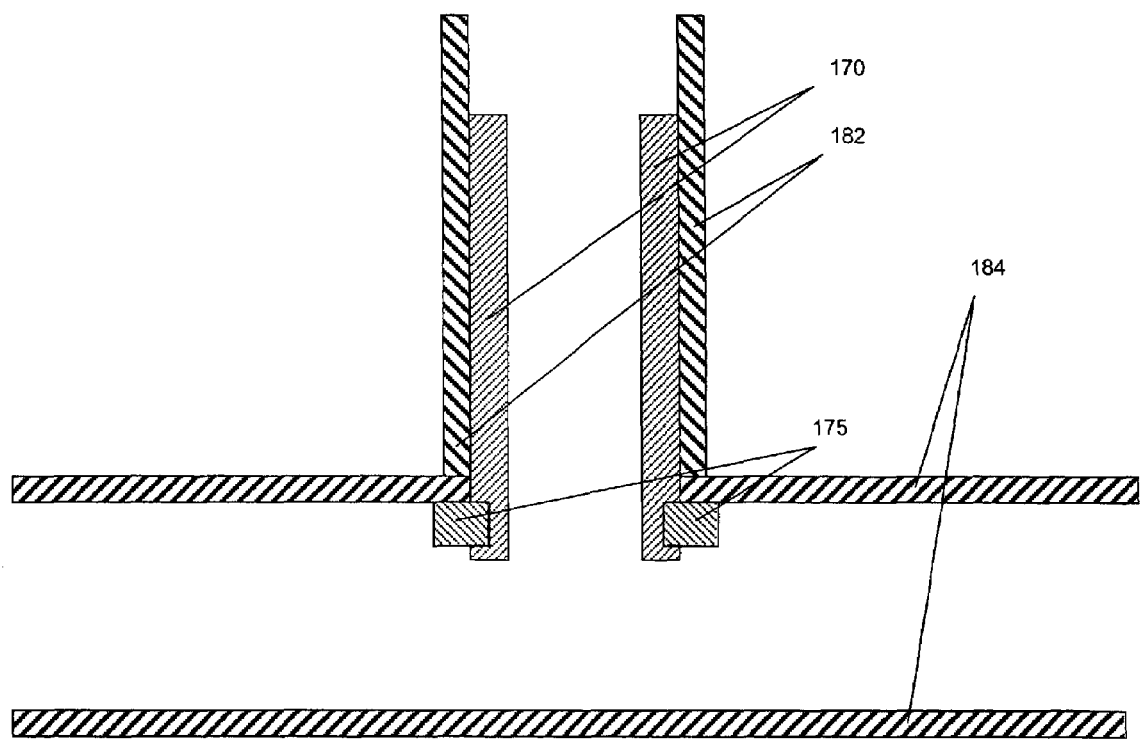

Referring again to FIGS. 13 and 14, once the connector engagement member 175 reaches the connector body 170, the connector engagement member 175 is positioned over the groove 170g of connector body 170. At this point, the voltage previously applied to the connector engagement member 175 is interrupted, resulting in radial contraction of the connector engagement member 175, such that connector engagement member 175 is firmly seated in the groove of connector body 170, at which point the anastomotic connector is fully deployed (see FIG. 14). As a result, the graft conduit 182 is secured to the aorta 184, forming an anastomotic connection between the two. Body fluid can henceforth flow between the aorta 184 and the graft conduit 182.

The anastomosis connector of the present invention is relatively small, which facilitates delivery and installation in the patient, even at relatively remote or inaccessible locations in the patient. For example, the connector body 170 can be delivered via relatively small-diameter instrumentation such as a cannula or laparoscopic-type device. Final installation of the connector engagement member 175 can be performed intravascularly using a delivery catheter and sheath as previously discussed. The connector therefore lends itself to use in less invasive or minimally invasive procedures.

The connector engagement member 175 in the above embodiment is in the form of a radially expandable and contractible ring. However, essentially any configuration that is capable of securely engaging the engagement member 175 to the connector body 170 can be used. For example, the connector engagement member 175 can include a plurality of radially expandable and contractible engagement arms like those illustrated above in connection with the filter element of FIGS. 9 and 10.

Moreover, in some embodiments, the electroactive polymer actuators are integrated into the connector body, rather than the connector engagement member. For example, a plurality of engagement arms can be provided on the connector body, with these arms being placed in a radially contracted position during insertion through the wall of the aorta. The arms can subsequently be introduced into the connector engagement member, whereupon the arms are placed in a radially expanded position, securely interlocking the two pieces. The appropriate voltage can be applied, for example, using a suitably modified laparoscopic device.

Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A filter apparatus for delivery over a guidewire within a tubular body conduit comprising:
   (a) a filter element transformable between a collapsed state and an deployed state, said filter element adapted to filter particulate matter from fluid within said tubular body conduit while in said deployed state; and
   (b) a locking member comprising one or more electroactive polymer actuators that switch said locking member between (i) a locking state wherein said locking member securely engages said guidewire and (ii) a release state wherein said locking member is movable along the length of said guidewire.

2. The filter apparatus of claim 1, further comprising a plurality of expandable and collapsible struts coupled to said filter element.

3. The filter apparatus of claim 1, wherein said locking member comprises a radially expandable and contractible annular member.

4. The filter apparatus of claim 1, wherein said locking member comprises one or more radially expandable and contractible arms.

5. The filter apparatus of claim 4, wherein said arms engage a guidewire indentation upon radial contraction of said arms.

6. The filter apparatus of claim 5, wherein said indentation is a circumferential groove.

7. The filter apparatus of claim 1, further comprising a delivery catheter that is adapted to apply a voltage to said locking member to switch said locking member between locking and release states.

8. The filter apparatus of claim 7, wherein said delivery catheter is provided with electrical contacts that correspond to complementary electrical contacts associated with said locking member.

9. The filter apparatus of claim 7, further comprising a tubular sheath adapted to receive said filter element when in said collapsed state.

10. A method of deploying a filter element within a tubular body conduit in a patient comprising:
    (a) providing the filter apparatus of claim 1;
    (b) advancing said filter apparatus over a guidewire within said tubular body conduit to a deployment position within said tubular body conduit, wherein said filter element is advanced while in said collapsed state;
    (c) switching said locking member from said release state to said locking state thereby engaging said locking member with said guidewire; and
    (d) expanding said filter element to said deployed state within said tubular body conduit.

11. The method of claim 10, wherein said locking member is a radially expandable and contractible member.

12. The method of claim 11, wherein said filter assembly is advanced over said guidewire while said locking member is in a radially expanded configuration and wherein said locking member is subsequently switched to a radially contracted position to securely engage said filter assembly to said guidewire.

13. The method of claim 10, wherein said tubular fluid conduit is a blood vessel.

14. The method of claim 13, further comprising conducting a procedure to treat said blood vessel upstream of said deployment position, wherein said filter element filters particulate matter dislodged by said procedure.

15. The method of claim 10, wherein said filter apparatus further comprises a delivery catheter slidably disposed along said guidewire, said delivery catheter being adapted to switch said locking member between said release state and said locking state.

16. The method of claim 10, wherein said filter assembly further comprises a tubular sheath slidably disposed along said guidewire and within which said filter element is delivered to said deployment position while in a collapsed state, whereupon said filter element reverts to said deployed state upon removal from said sheath.

\* \* \* \* \*

UNITED STATES PATENT AND TRADEMARK OFFICE
CERTIFICATE OF CORRECTION

| | | |
|---|---|---|
| PATENT NO. | : 6,969,395 B2 | Page 1 of 1 |
| APPLICATION NO. | : 10/213993 | |
| DATED | : November 29, 2005 | |
| INVENTOR(S) | : Alan David Eskuri | |

It is certified that error appears in the above-identified patent and that said Letters Patent is hereby corrected as shown below:

Col. 1, line 51, change "2002/0,022,858" to - - 2002/0022858 - -.

Col. 1, line 52, change "2002/0,045,916" to - - 2002/0045916 - -.

Col. 1, line 53, change "2002/0,004,667" to - - 2002/0004667 - -.

Col. 1, line 54, change "2001/0,012,951" to - - 2001/0012951 - -.

Col 3, line 15, after "present", insert - - invention - -.

Col 3, line 35, after first word "is", insert - - that - -.

Col. 3 line 38, after first word "is", insert - - that - -.

Col. 5, line 14, after "of", delete - - the - -.

Col. 10, line 38, after "if", insert - - a - -.

Col. 11, line 2, change "griped", to - - gripped - -.

Col. 11, line 5, before first word "applied", insert - - be - -.

Col. 12, line 6, change "an", to - - a - -.

Signed and Sealed this

Eighth Day of August, 2006

JON W. DUDAS
*Director of the United States Patent and Trademark Office*